United States Patent
Giaquinta et al.

(10) Patent No.: US 6,292,983 B1
(45) Date of Patent: Sep. 25, 2001

(54) ADJUSTABLE QUICK-RELEASE BUCKLE, PARTICULARLY FOR DIVING MASKS OR SIMILAR

(75) Inventors: Ciro Giaquinta, S. Colombano Certenoli; Fabio Testa, Busalla, both of (IT)

(73) Assignee: Tecnorubber S.r.l., S. Colombano Certenoli (IT)

( * ) Notice: Subject to any disclaimer, the term of this patent is extended or adjusted under 35 U.S.C. 154(b) by 0 days.

(21) Appl. No.: 09/508,895
(22) PCT Filed: Jul. 1, 1998
(86) PCT No.: PCT/EP98/04071
  § 371 Date: Mar. 20, 2000
  § 102(e) Date: Mar. 20, 2000
(87) PCT Pub. No.: WO99/02059
  PCT Pub. Date: Jan. 21, 1999

(30) Foreign Application Priority Data

Jul. 11, 1997 (IT) ............................... SV97A0037

(51) Int. Cl.[7] ............... A44B 11/00; A44B 11/25
(52) U.S. Cl. ................. 24/68 R; 24/163 R; 24/265 BC; 24/69 ST
(58) Field of Search ............... 24/68 R, 69 ST, 24/68 SK, 265 C, 265 BC, 163 R, 909, 265 B; 2/426, 450, 452; 441/64; 351/41, 43

(56) References Cited

U.S. PATENT DOCUMENTS 2,537,307 * 1/1951 Griswold ................ 24/170
4,607,398 * 8/1986 Faulconer ................ 2/452
5,555,571 * 9/1996 McCaffrey ................ 2/428
5,588,186 * 12/1996 Ko ........................ 24/585
5,611,644 * 3/1997 Lutz ...................... 405/186

FOREIGN PATENT DOCUMENTS 195 20 981-
   A1 * 1/1996 (DE) .

* cited by examiner

Primary Examiner—James R. Brittain
Assistant Examiner—Ruth C. Rodriquez
(74) Attorney, Agent, or Firm—James Creighton Wray; Meera P. Narasimhan

(57) ABSTRACT

An adjustable quick-release buckle, particularly for masks or similar, of the type provided in combination with a strap (1). The strap has a set of equally spaced teeth (101), projections, transverse ribs, or similar, arranged along the strap (1), and at least on the end portions of said strap (1), covering a predetermined length, and the buckle (2) has removable means (4, 5), preventing the strap (1) from sliding in the loosening direction, and allowing it to slide in the opposite tightening direction, said means (4, 5) being controllable, when the strap (1) is in the disengagement position, also in said loosening direction. According to the invention, the means for retaining the strap (1), designed to allow it to slide in one direction, and to prevent it therefrom in the opposite direction, consist of removable means (4, 204, 5, 105, 205, 305), which are elastically loaded and do not act directly on the strap (1), but cooperate with guide means (4, 104, 204) engaged with its teeth, projections, ribs or similar (101).

14 Claims, 2 Drawing Sheets

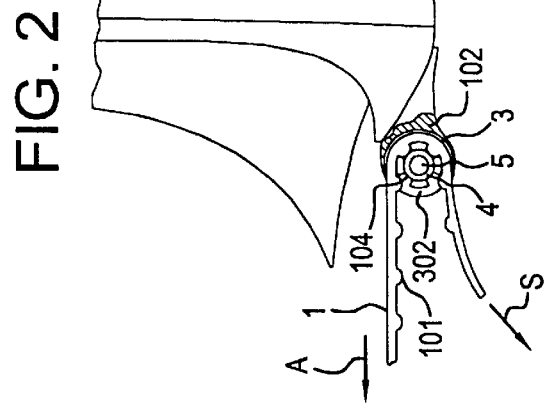
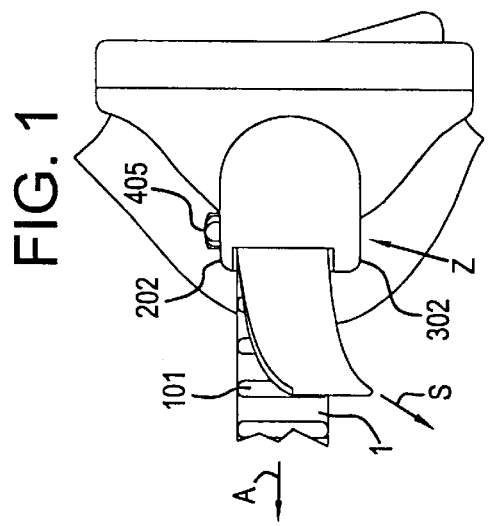
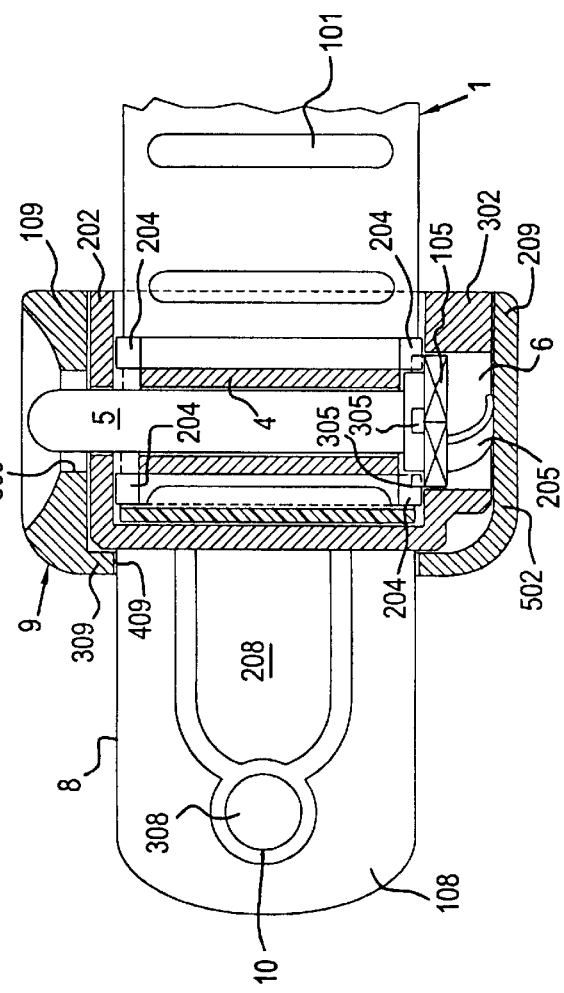

ADJUSTABLE QUICK-RELEASE BUCKLE, PARTICULARLY FOR DIVING MASKS OR SIMILAR

BACKGROUND OF THE INVENTION

The invention relates to an adjustable quick-release buckle, particularly for masks or similar, of the type provided in combination with a strap.

At present, as disclosed for example in U.S. Pat. Nos. 4,607,398, 5,611,644, 5,555,671 and DE 195 20 981, particularly in diving masks, buckles of the type described hereinbefore are used, which allow the strap to be stretched to tighten the mask, by simply exerting a pulling action in that direction on the free ends of the strap, which project out of the buckle, whereas the strap is loosened by manually acting on the release means, which bring the retaining means to temporary disengagement from the strap.

These buckles have a member for returning the strap, which return member brings the strap into cooperation with one retaining tooth. The return member also acts as an abutment member cooperating with the retaining tooth. The tooth has an asymmetrical profile, i.e. is provided with guide slanted surfaces, which help the strap to slide in the tightening direction, preventing it therefrom in the opposite direction, while said tooth is provided at the free end of a wing which is mounted in such a way as to be able to swing about an axis in the middle of and substantially parallel to the projections on the strap. The wing is elastically and stably loaded by a spring in order to press the tooth against the strap, i.e. against the return member.

This construction, though rather effective and convenient as regards strap tightening, always requires a certain effort which, on use, may involve a possible displacement of the mask from its correct wearing position. However, on releasing the strap, for example to take off the mask, the above well-known construction is quite unsuitable, inconvenient and involves the use of both hands. In order to bring the tooth into disengagement from the toothed end of the strap, the wing must be pressed against the force of the elastic means. This wing is generally disposed parallel to the temple or to the nearby zone, so a certain pressure action is to be exerted against the temple. At the same time, it is necessary to act on the strap, to help or assist its sliding movement inside the buckle in the loosening direction.

SUMMARY OF THE INVENTION

U.S. Pat. No. 5,588,186 discloses a buckle showing the combination of features of the preamble of claim 1. The belt has a pawl assembly vertically held between the top and bottom walls of the buckle and selectively engaging with a ratchet part. The pawl assembly has a rotatable cylinder, a pawl coupled to the cylinder and adapted for selectively engaging with the ratchet part. A vertically movable push rod is received in the cylinder such that the bottom of the push rod projects out of the bottom wall of the bucket. The cylinder along with the pawl is rotated to make the pawl disengage from the ratchet part when the push rod vertically moves up in the cylinder. In order to rotate the cylinder with the pawl, a radial projection of the push rod is received in an inclined slit formed on a side wall of the cylinder.

The invention has the object to provide a buckle of the type described hereinbefore, in such a way that, by means of simple and cheap arrangements, the tightening and loosening operations are made simpler, quicker and more convenient, while providing that said operations may be accomplished by one hand only, and while ensuring the highest functional reliability of the buckle.

The invention achieves the above purposes by providing a buckle of the type described hereinbefore, sewing the combination of features according to the characterizing part of claim 1.

The further sub claims disclose further improvements of the general idea of the invention according to claim 1.

The claimed features clearly show the advantages of the present invention. On one side, the very simple construction and the absence of the difficult-to-operate tooth on the swinging wing, which makes even the free strap-tightening operations troublesome. The sliding movement of the strap is ensured by the rotation of the roller, acting as a toothed crown, therewith, while limiting all sliding frictions which are relatively high, due to the type of materials generally used, such as rubber, or others. On the other hand, by increasing the number of teeth or projections on the strap and on the roller, an adjustment with shorter pitches, and hence better calibrated and accurate, of the tightening tension of the strap may be provided.

Finally, in order to loosen the strap, a little axial movement between the ratchet-like means and the roller is only needed. Such an axial movement is more favorable per se and can be performed more easily by one hand, for obvious anatomic reasons. Since the buckle projects out of the mask body, or of any other object, a grasping movement of the fingers of one hand is possible. Further, the particular embodiment allows the provision of elastic means for holding the roller and the ratchet-like means stably coupled, which do not require considerable forces and hence may be easily opposed by only exerting a little force.

When the roller is released also with respect to the strap-loosening direction of rotation, the resistance to the sliding movement to move them apart is very little, therefore the other hand is not required to exert actions to assist said sliding movement in the strap-loosening direction of the strap, but this movement for moving the mask away from the face involves the strap to simultaneously slide in the loosening direction.

The invention also relates to further characteristics, which form the subject of the dependent claims.

The characteristics of the invention and the advantages derived therefrom will appear more clearly from the following description of an example, illustrated in the accompanying drawings, in which:

BRIEF DESCRIPTION OF THE DRAWINGS

FIG. 1 is a side view of a mask with a buckle according to the invention.

FIG. 2 is a top view of the mask as shown in FIG. 1, the buckle area being shown in a cross sectional view.

FIG. 4 is an axial section of the buckle as shown in FIG. 3.

DETAILED DESCRIPTION

Figure 3:
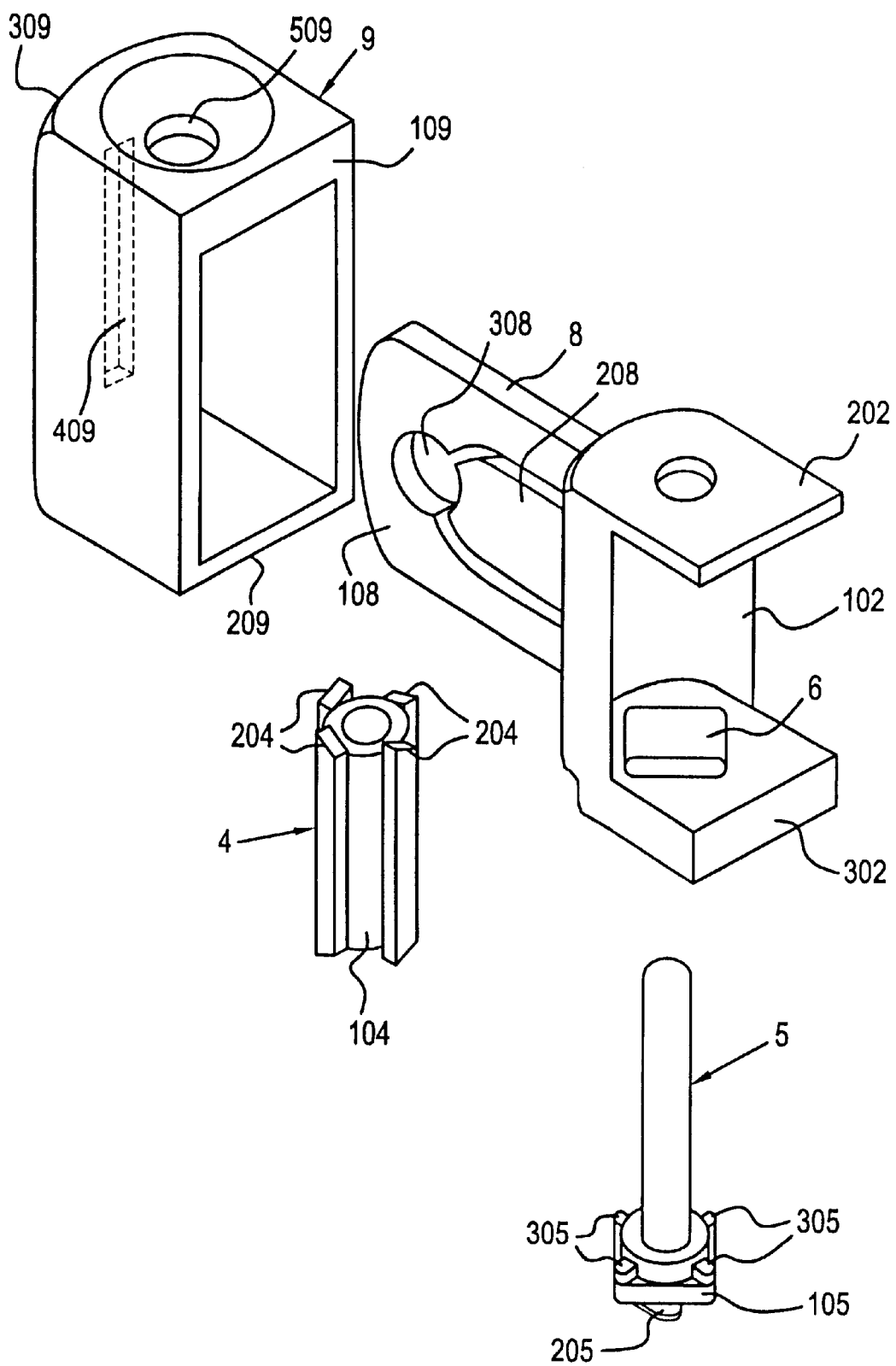
FIG. 3 is an exploded view of a variant embodiment of the buckle according to the invention.

Referring to the figures, a buckle according to the invention, of the type designed to allow a strap 1 to be progressively tightened and loosened only on control thereof, comprises a buckle body 2, wherein a return duct 3 is provided. The duct has an arched shape, especially angularly extending over about 180°, and is formed by a radially outer wall 102 and by a radially inner wall. The two walls are substantially concentric and the distance therebetween substantially corresponds to or is slightly greater than the thickness of the strap 1, so as to allow the latter to slide inside the duct 3. The strap 1 has, at least on its radially inner face, a plurality of teeth, ribs, or similar 101, which are oriented transverse to the longitudinal axis of the strap 1.

The radially inner wall of the return duct 3 consists in the curved surface of a roller 4, which is mounted so as to be rotatable substantially coaxial to the radially outer wall 102.

The roller 4 has a plurality of grooves 104, formed in its curved surface, which extend for the whole of its axial length and are angularly equally spaced. The grooves 104 are at such a distance from each other that the arc of a circle therebetween corresponds to the distance between the individual teeth 101 of the strap 1, and their shape and cross section correspond to that of the teeth 101, so that the latter can be engaged with the grooves 104 of the roller 4.

Obviously, the conformation of the strap 1, and particularly the shape and size of the teeth and the pitch therebetween is substantially complementary or corresponding to the outer shape of the roller, that is to the shape of the groove or of the peripheral radial teeth 104 of the roller 4, to the size thereof, and to the angular distance between said teeth or said grooves 104, so that the roller 4 is always dynamically engaged with the strap 1.

The roller 4 is rotatably mounted on an axis, consisting of a central pin 5, which is supported, in such a way as to be unable to rotate but able to slide axially to a certain predetermined extent, in two transverse end walls 202, 302, integral to the buckle body 2.

An end wall 202 has a round hole for housing one end of the central pin 5, being meant to project out of it. The other end wall 302 has a coaxial notch 6, which is closed on the outer side of the buckle and has a non-round section. The end of the central pin 5 being meant to be held in the non-round seat 6 is made in the form of a complementarily non-round shaped small base 105. The non-round notch or seat 6 in the transverse wall 302 is axially longer than the axial extension of the non-round small base 105 of the central pin 5, whereas the latter is axially slidable inside the notch 6, there being provided, between the closed end wall of the notch 6 and the facing end of the small base 105, an elastic element 205. This element preferably, but not necessarily consists of an elastic tongue which extends from a peripheral edge of the small base, while being integral therewith, to the area of the central axis thereof, or up to the opposite edge, taking the form of a bridge of material, which is outwardly arched in the axial direction of the central pin 5. There may be obviously provided other types of elastic means, such as a spring or similar. The choice in the embodiment is anyway preferable, since it reduces the number of parts forming the buckle, avoiding the use of metal parts, exposed, for example, to the attacks of salt water and providing a simpler assembly of the buckle, hence reducing manufacturing costs.

In the peripheral area of the small base 105, projecting, in the form of a step, out of the curved surface of the central pin 5, on the side of said base 105, facing the opposite end of the central pin 5 and axially superposing the end edge of the roller 4, particularly in the corner areas of the roller surface facing the opposite end of the central pin 5, there are provided at least one axial tooth 305, particularly four angularly equally spaced axial teeth 305. Said teeth cooperate with axial teeth 204 on the facing end side of the roller 4, which teeth are asymmetrical, or saw-toothed, having a steeper substantially axial arm and a less steep arm, acting as a guide slanted surface. The axial teeth 204 on the end side of the roller 4, facing the small base 105 of the central pin 5 are oriented in such a manner that the less steep fronts, acting as guide surfaces face the strap-tightening direction, as indicated by arrow S, whereas the steeper, substantially axial ones, face the strap-loosening direction. The pitch of the axial teeth 204 of the roller 4 and of the retaining teeth 305 on the small base 5 is such that each jerk corresponds to a forward step, which is equal to the forward step of one tooth 101 of the strap 1 or to fraction of said step.

By pulling the end of the strap 1 in the tightening direction S, the strap 1, engaged by its teeth 101 in the grooves 104 of the roller 4, drags the latter into rotation. In this case, the axial teeth 305 of the small base 105 are assisted by the less steep guide fronts of the axial teeth 204 of the roller 4. Hence, the small base 105 and the central pin 5 are axially pushed against the action of the elastic means 305 towards the non round seat 6, associated to the wall 302 of the buckle 2, and so the roller may freely advance, in a jerky motion, in the strap-tightening direction of rotation S. After each forward step, the axial teeth 305 of the small base 105 of the central pin 5 pass to an engagement position behind the steeper front of the corresponding axial tooth 204 of the roller 4, thus ensuring that the tightening condition achieved is locked.

The roller 4 generally abuts by its end side opposite to the small base 105, against the inner side of the wall 202, in such a way that any undesired axial movement thereof on the pin 5 can compromise the engagement of the axial teeth 204 of the roller 4 with the axial retaining teeth 305 of the central pin 5.

By exerting a pulling action on the strap 1 in the loosening direction thereof, following arrow A, the axial fronts of the axial teeth 204 of the roller 4 abut against the facing axial fronts of the axial teeth 305 on the small base 105 of the central pin 5, therefore the roller is locked with respect to a direction of rotation corresponding to the strap-loosening direction and so is the strap 1, which is mechanically engaged with the roller 4.

In order to unlock the roller so that the strap 1 can be loosened, the end of the central pin 5, opposite to the small base 105, and projecting out of the transverse supporting wall 202 is only to be pressed. The pressure action, oriented axially towards the small base 105 and against the action of the elastic means 205, causes the central pin 5 to slide with respect to the roller 4, in order to move the small base 105 away from the facing end side of the roller 4, thereby disengaging the retaining teeth 305 on the small base 105 from the axial teeth 204 on the end side of the roller 4. Under these conditions, the roller 4 is free to rotate about its axis also in the strap-loosening direction, and the strap is free to rotate inside the duct 3, in the loosening direction A.

The free button-like end of the central pin 5, may be also associated to further elastic means, acting in the same directions as those provided between the non round base 105 and the notch or seat 6 in the wall 302. In this case, as shown in FIG. 1, said means consist of a plurality of tongues, forming a sort of cage around the free end of the pin 5, or a sort of cap, indicated as 405.

The above description clearly shows the advantages of the present invention. What appears first is the remarkable simplicity and inexpensiveness of the parts composing the buckle 2. These may be all manufactured as molded plastic parts, therefore made of an almost unperishable, long-life material, generally little affected by the attacks of agents like salt water, or else.

The considerable simplicity of the parts composing the buckle obviously affects the operational reliability and life, as well as the assembly simplicity of the buckle.

Moreover, the buckle does not require particular straps specific for the purpose, but the usual strap currently in use may be used therewith.

The construction of the buckle according to the invention allows to enjoy a considerable freedom in the exterior conformation thereof, there being required only one semicircular duct, delimited by a semicircular or arched wall, which is axially provided with two transverse extensions, supporting the central axis 5 with the parts 105 annexed thereto.

Finally, the construction does not have excessive space requirements, on the contrary it can be fabricated of a size at least equal to, substantially slightly smaller than the usual buckles.

Functionality and convenience of use are apparent from what has been described herein. The roller 4 allows the strap 1 to be accurately adjusted and securely locked in the desired position.

The strap may be easily unlocked in the loosening direction A by a grasping movement of the hand, for example by a forefinger and a thumb, thanks to the two walls 202 and 302. The wall 302 acts as an abutment, when pressure is exerted on the head of the central pin 5. Therefore, no body part is to be used as an abutment, thus avoiding painful and inaccurate actions and often, depending on the specific body part, unstable abutment functions, which do not ensure the correct operation of the unlocking means.

Since the strap 1 is guided in its sliding movement in an arched return duct 3, one of whose walls is the roller, being pressed against it by tension thereon, said sliding movement of the strap 1 in the duct 3 both for tightening it and, in the roller unlocked condition, for loosening the strap, is substantially friction-free, or anyway subject to a very little friction, so that the effort for pulling the strap substantially consists in the elastic tension on the roller and in overcoming the elastic means 205 for the jerky motion of the roller 4, whereas in the loosening direction, with the roller in the unlocked position, the strap slides freely, and can be loosened while the part tightened by the strap, for example the mask, is put off and moved apart.

Hence, in the case shown in FIGS. 1 and 2, once the two end surfaces 202 and 302 are grasped and pressed between the forefinger and the thumb of one hand, while pressure is exerted on the central axis 5, the mask is removed, by simply loosening the strap while it is moved away from the face, and simply by grasping the mask by said two fingers on the buckle.

A further advantage of the present invention consists in that the same parts may be used to provide two opposite buckles, for example to the right and to the left of a mask, or similar. The parts composing the buckles are substantially identical, while the only part needing a modification, due to the inversion of the tightening and loosening directions is the roller 4, i.e. the axial teeth 204 thereof. However, to this end, as shown in the figures, the roller may have axial teeth 204 on both end sides, the orientation of the axial teeth 204 on the two opposite end sides of the roller 4 being symmetrically identical, with reference to a radial median plane of the roller 4. Therefore, in order to obtain the right or left buckle, for example in the mask shown in FIG. 2, the roller 4 need only be mounted with the right orientation.

Another advantage, particularly obtained when the strap is used to tighten parts of the human body, for example in a mask, is that, unlike in the case of known masks, the strap adheres to the body with its completely smooth face, the teeth, projections, ribs, or similar 101 being only provided on the outer side, facing the roller.

The conformation flexibility of the buckles according to the invention is apparent from the two variant embodiments as shown.

With reference to FIGS. 1 and 2, the buckle according to the invention is provided on a diving mask. In this case, from the rigid frame of the mask, in the vertical side areas thereof, two extensions made of one piece therewith, or welded, glued or anyhow fixed thereto develop, said extensions being shaped in such a manner as to form on the rear side with reference to the wearing position, a substantially semi-cylindrical notch, with spaced end walls 202 and 302. In these walls 202 and 302 there are provided apertures for the passage of the button-like head of the central pin 5, and a non-round notch 6 for the base 105 of the central pin 5.

To make the assembly even easier, the wall 302 has a through hole which forms the side walls of the notch 6, whereas the end wall forming the closed side of the notch 6 is snap-fitted, glued, and welded later.

The assembly is very simple. The central pin 5 is inserted from the outer side of the associated transverse wall 302 through the hole which forms the side walls of the notch 6, and the roller 4 is slipped thereon, while passing it in the area between the two transverse end walls 202 and 302. Once the central pin 5 is inserted in its correct position, with the roller thereon, the notch 6 is closed from the outside by applying a cover 502 on the outer side of the wall 302.

FIGS. 3 and 4 show a variant embodiment, providing the use of the buckle according to the invention also in combination with other types of objects, such as fins, or else.

In this case, the buckle body 2 has a forked construction, wherein a fastening plate 8 is connected to a fork, comprising an arched wall 102, with two transverse walls 202 and 302 extending from its end sides. The former transverse wall has one hole for the outward passage of the button-like end of the central pin 5, whereas the opposite transverse wall 302 has a non-round hole which forms the side walls of the notch 6 for the non-round small base 105 of the central pin 5.

The buckle is closed sideways by a cap 9, which forms the side walls and has walls, indicated as 109, 209 in FIGS. 3 and 4, outwardly superposing the transverse walls 202 and 302, besides having an arched wall 309 which outwardly superposes the arched wall 102, a slot 409 being provided therein for the passage of the fastening plate 8. The cap side being opposite to the arched wall 309 is completely open and acts as an entry and an exit for the strap 1, in its return path around the roller 4.

The wall 209 which outwardly superposes the wall 302 forms the axial bottom for closing the notch or seat 6, for the non round base 105 of the central pin 5, whereas the wall 109 superposing the operating head on the central pin 5, has a hole 509 which, when the cap 9 is in the mounted condition, is coincident with the hole formed in the wall 202, and through which the head of the central pin 5 projects outwards. The wall 109 of the closing cap 9 may be possibly provided, on its outer side, with an anatomic shape, for example with a little concave recess, coaxial to the through hole for the central pin 5.

Thanks to the fact that the parts are made of plastic, and therefore of an elastic material, and to the fact that the central pin 5 may be inserted axially with respect to the wall 202 and 109, the closing cap 9 may be force-fitted on the part 2.

The fastening plate 8 may be of any type, simply meant to be welded, glued or fixed by screws or other means. In the illustrated embodiment, it is of the type provided in combination with wide-head hooking pins, like those provided on the sides of fin footpockets, or the like.

Particularly, the plate 8 has a peripheral U-shaped part 108, surrounding a median tongue 208, the ends of the peripheral U-shaped part 108 and the central tongue 208 being fastened to the arched part 102. A hole 308 is provided on the plate 8, in such a position that the peripheral edge of said hole is partially formed by the U-shaped part 108 and partially by the central tongue 208. By this arrangement, the hole 308 may be elastically opened apart, for the passage of the wide head of the buckle-hooking pin 10.

The illustrated embodiments are only two preferred examples of the buckle according to the invention, showing its remarkable versatility both in use and in conformation.

The buckle is particularly intended to be used in combination with diving masks, but the use thereof is not limited thereto, and may be provided in combination with any strap, which has to be continuously tightened and unlocked on control in the loosening direction.

The materials used to fabricate the buckle may also be of other types, depending on the field of use.

Obviously, the invention is not limited to the embodiments described and illustrated herein, but may be greatly varied, especially as regards construction, without departure from the guiding principle disclosed above and claimed below.

What is claimed is:

1. A combination of an adjustable quick-release buckle and a strap which has a set of equally spaced teeth, arranged on at least one end portion of said strap, particularly for masks, which combination comprises:
   a) a buckle body;
   b) a return roller rotatably mounted on the buckle body and around which passes the strap;
   c) a ratchet strap retaining means mounted in a displaceable way on the buckle body and urged by elastic means in a direction of an active position, in which said ratchet means prevent the strap to slide in a loosening direction allow it to slide in opposite tightening direction;
   d) means for manually displacing the ratchet means against the action of the elastic means in an inactive position, in which said ratchet means allow the strap to slide freely in both the loosening direction and the tightening direction;
   characterized in that
   e) the buckle body has an arched wall, which extends coaxial to the roller through a certain angular width, a distance between the arched wall and the roller substantially corresponding to or being slightly greater than a thickness of a strap, but smaller than the total thickness of the strap including a projection of the teeth of the strap;
   f) the return roller has longitudinal external teeth and a strap is passed between the roller and the arched wall of the buckle body so as to engage the teeth of the strap between the teeth of the roller;
   g) the return roller is rotatably mounted on a central pin, the pin bears at one of its ends at least one axial locking tooth, the tooth cooperates with a crown of axial teeth on a facing end side of the roller, the teeth have a guide slanted side facing a strap tightening direction of rotation, and a substantially axial steep front on the side facing a strap loosening direction of rotation, wherein the pin is mounted in such a way as to be unable to rotate but to be able to slide axially to move the locking tooth from the crown of axial teeth on an facing end side of the roller, while opposing the action of elastic means which stably push said pin towards engagement of the locking tooth with the teeth of the end side of the roller, said pin projecting out of a transverse wall of the buckle with a button head.

2. A combination as claimed in claim 1, characterized in that the pin is mounted in two transverse walls (202,302) connected to axial ends of the arched wall (102), the roller (4) being interposed therebetween, wherein a transverse wall (202) has a round hole through which a button end of the pin (5) projects out of an outer side of said wall, and an opposite transverse wall (302) has a non round guide notch (6) allowing a corresponding end (105) of the central pin (5), shaped as a non-round base, complementary to the notch (6), to slide axially therein, the notch (6) being closed on a side opposite to the roller (4), an elastic means provided between a bottom of the notch (6) and a facing end side of the non round base (105) of the central pin (5), for pressing said base against the end side of the roller (4).

3. A combination as claimed in claim 2, characterized in that in areas of the non round base (105) projecting out of a peripheral curved surface of the center pin (5), there are provided one or more axial teeth (305).

4. A combination as claimed in claim 2, characterized in that the elastic means for pressing the non round base (105) of the central pin (5) consist of extensions (305) made of one piece with said base (105).

5. A combination as claimed in claim 4, characterized in that the elastic means (205) associated to the non round base (105) of the central pin (5) consist of at least one radial tongue of material, or of at least one transverse bridge, which extend from a peripheral edge of the end side of the base (105), opposite to the roller (4), and are made of the same material as the pin (5) and/or the base (105).

6. A combination as claimed in claim 2, characterized in that the buckle body (2) is integral, made of one piece with, welded or glued, to a part to be connected to an strap (1), there being provided a closing cover (502) of the open end side of the non round guide notch which forms axial side walls substantially the notch (6) in the transverse wall (302), said cover being stably attachable by welding, gluing to an outer side of the transverse wall (302) or being removably attachable by mutual snap-fitting means.

7. A combination as claimed in claim 2, characterized in that the arched wall (102) and the transverse walls (202, 302) for supporting the central pin (5) with the roller (4) are made of one piece with a rigid frame of a diving mask, and have a form of lateral extensions.

8. A combination as claimed in claim 1, characterized in that the roller (4) has axial teeth on the two end sides, axial teeth (204) on a two end sides being oriented with less steep fronts in the same direction.

9. A combination as claimed in claim 8, characterized in that a closed outer side of the opposite transverse wall (302) of the buckle body (2), provided with the notch (6) for housing the non round base (105) of the central pin (5), has a non round through hole, forming side walls of the notch (6), and a closing wall (209, 502), forming the bottom side of the notch (6), and being attachable to the transverse opposite wall (302), acting as an abutment wall for pressure movement of the central pin (5) exerted by two grasping fingers.

10. A combination as claimed in claim 8, characterized in that a bottom wall (209) of a cap (9) substantially parallel to the opposite transverse wall (302), associated to the non round base (105) of the central pin (5) is an end wall of the cap (9) which outwardly superposes the arched wall (102)

and associated transverse walls (202, 302), which cap has, on an side opposite to an arched wall of the cap (309), outwardly superposing the arched wall (102), an aperture for elastically force-fitting the assembly composed of the arched wall (102), of the transverse walls (202, 302), and of the central pin (5), with a roller (4) in the position it takes when it is fitted in the transverse walls.

11. A combination as claimed in claim 1, characterized in that there are provided elastic means (405) also at a projecting button end of the pin (5).

12. A combination as claimed in claim 1, characterized in that it is provided in combination with a wide-head hooking pin (10), integral to the body whereto the buckle is to be attached, the arched wall of the buckle body (2) being associated to means (8) for removable engagement to said pin (10).

13. A combination as claimed in claim 12, characterized in that the means for removable attachment to the wide-head hooking pin (10) consist of a fastening plate (8), with a hole (308), which fastening plate (8) is composed of a frame part (108) and of a flexible central tongue (208), an edge of the hole (308) being formed partially by a shaped side of the flexible central tongue (208) and by the frame part (108) surrounding at least three free ends of the flexible central tongue (208).

14. A combination as claimed in claim 13, characterized in that the fastening plate (8) is provided in combination with other means for attachment to the body associated to the buckle.

* * * * *